(12) United States Patent
Gerlitz

(10) Patent No.: US 10,585,291 B2
(45) Date of Patent: Mar. 10, 2020

(54) EYE SAFETY SYSTEM FOR LASERS

(71) Applicant: Yonatan Gerlitz, Lev Hasharon (IL)

(72) Inventor: Yonatan Gerlitz, Lev Hasharon (IL)

( * ) Notice: Subject to any disclaimer, the term of this patent is extended or adjusted under 35 U.S.C. 154(b) by 0 days.

(21) Appl. No.: 15/964,029

(22) Filed: Apr. 26, 2018

(65) Prior Publication Data

US 2018/0314070 A1 Nov. 1, 2018

Related U.S. Application Data

(60) Provisional application No. 62/491,525, filed on Apr. 28, 2017.

(51) Int. Cl.
*G02B 27/09* (2006.01)
*G02B 27/14* (2006.01)
*A61F 9/02* (2006.01)
*F21Y 115/30* (2016.01)
*A61B 90/00* (2016.01)

(52) U.S. Cl.
CPC ............ *G02B 27/0955* (2013.01); *A61F 9/02* (2013.01); *A61F 9/029* (2013.01); *G02B 27/141* (2013.01); *A61B 2090/049* (2016.02); *F21Y 2115/30* (2016.08)

(58) Field of Classification Search
CPC ....... G02B 27/01–0189; G02B 2027/01–0198; G03B 21/2086; A61B 2090/049
See application file for complete search history.

(56) References Cited

U.S. PATENT DOCUMENTS

| | | | |
|---|---|---|---|
| 4,543,477 A | 9/1985 | Doi et al. | |
| 5,323,269 A | 6/1994 | Walker et al. | |
| 5,451,765 A * | 9/1995 | Gerber | B23K 26/032 |
| | | | 219/121.62 |
| 5,837,996 A | 11/1998 | Keydar | |
| 2003/0021672 A1 | 11/2003 | Sinofsky | |
| 2012/0224142 A1* | 9/2012 | Cornsweet | A61B 3/12 |
| | | | 351/206 |
| 2014/0009367 A1* | 1/2014 | Lvovskiy | G02B 27/017 |
| | | | 345/8 |
| 2015/0289762 A1* | 10/2015 | Popovich | G02B 27/0093 |
| | | | 351/209 |
| 2016/0062121 A1* | 3/2016 | Border | G02B 27/0172 |
| | | | 359/630 |
| 2016/0338586 A1* | 11/2016 | Sun | A61B 3/107 |
| 2017/0001402 A1 | 1/2017 | Guyton et al. | |
| 2017/0147859 A1* | 5/2017 | Zhang | G02B 27/0093 |
| 2018/0164583 A1* | 6/2018 | Wall | G02B 27/0018 |

\* cited by examiner

*Primary Examiner* — Cara E Rakowski
*Assistant Examiner* — Christopher A Lamb, III
(74) *Attorney, Agent, or Firm* — Rod D. Baker

(57) ABSTRACT

An eye safety system, based on retro-reflection from the eye, to shut off a laser source in a short time to avoid approaching the hazard level of the eye. In the event of an accidental direction of laser light toward a nearby eye, the system rapidly collects and detects laser light that retroflects from the retina of the eye. Upon detecting the retroflected light, a comparator/processor assembly signals to switch off the laser source to terminate the hazard to the eye.

14 Claims, 1 Drawing Sheet

EYE SAFETY SYSTEM FOR LASERS

CROSS-REFERENCE TO RELATED APPLICATIONS

This application claims the benefit of the filing of U.S. Provisional Patent Application Ser. No. 62/491,525 filed 28 Apr. 2017 and entitled "Eye Safety Mechanism for Lasers," the entire contents of which are incorporated herein by reference. This application is related to U.S. Pat. No. 9,946,082, entitled "Handheld, Low-Level Laser Apparatuses and Methods for Low-Level Laser Beam Production," issued 17 Apr. 2018, and to U.S. Pat. No. 9,553,422 entitled "Multiple Aperture Hand-Held Laser Therapy Apparatus," issued 24 Jan. 2017. Each patent is incorporated herein by reference in its entirety.

BACKGROUND OF THE INVENTION

Field of the Invention

The invention relates generally to eye safety, particularly to methods and apparatuses for protecting eyesight from harm due to laser light, and specifically to a system and method to shut off a laser source to prevent eye damage.

Description of Related Art

The devices in U.S. Pat. No. 5,451,765 to Gerber capture scattered light from the surface of an object to detect whether the object is in the path of a laser. The Gerber patent describes energy scattered upon striking an object, and refers to some of the scattered energy as reflected energy, when reflected back along the laser beam optical axis. However, FIGS. 1-3 of Gerber show that the reflected energy is not limited to the energy retro-reflected parallel to the laser path, but that the device also captures scattered light that is returned but which is not parallel to the laser path. Accordingly, Gerber's device is unable to distinguish light retro-reflected from a potentially endangered eye, as opposed to scattered light from other surfaces.

SUMMARY OF THE INVENTION

This system and apparatus may be integrated as a safety feature into many of various laser light-emitting devices, so to shut off a laser source to prevent eye damage. A laser source produces a laser beam which passes through one or more lenses to collimate the divergent beam. A dichroic beam splitter is centered on the optical axis of the collimated laser beam. The portion of the beam not reflected by the first side of beam splitter passes through the dichroic beam splitter and is expanded and collimated in one or more additional lenses. The dichroic beam splitter reflects a narrow wavelength band that includes the laser emission wavelength.

Any light retroflected from a threatened eye returns to the beam splitter. The beam splitter is placed to reflect the retro-reflected light into a collecting eye safety lens with an infinity focus (infinity conjunction) designed to collect and direct the retro-reflected light onto a fast detector. The dichroic beam splitter reflects a fraction of the retro-reflected light into the eye safety lens. Because the beam splitter is dichroic, it reflects only a narrow wavelength band (that includes the laser emission wavelength) into the eye safety lens.

The eye safety lens has a screened small aperture (e.g., having a diameter approximating the average diameter of the pupil of an adult eyeball in medium light), and may be designed for an infinity-focused retro-reflected beam, that is, a beam composed mainly of parallel rays. The small aperture and infinity conjunction of the eye safety lens capture almost only light retro-reflected from an eye, and reduce the capturing of scattered light unassociated with the retroflection. The eye safety lens directs retroflected light to a fast detector. The detector is connected to an amplifier and comparator to identify the retro-reflected signal. Once a signal is identified, the eye safety mechanism stops laser emission from the source to terminate the laser threat to the eye.

BRIEF DESCRIPTION OF THE DRAWING

The foregoing and additional features and characteristics of this disclosure will become more apparent from the following detailed description considered with the reference to the accompanying drawings, wherein.

DETAILED DESCRIPTION OF THE INVENTION

Figures 1, 2:
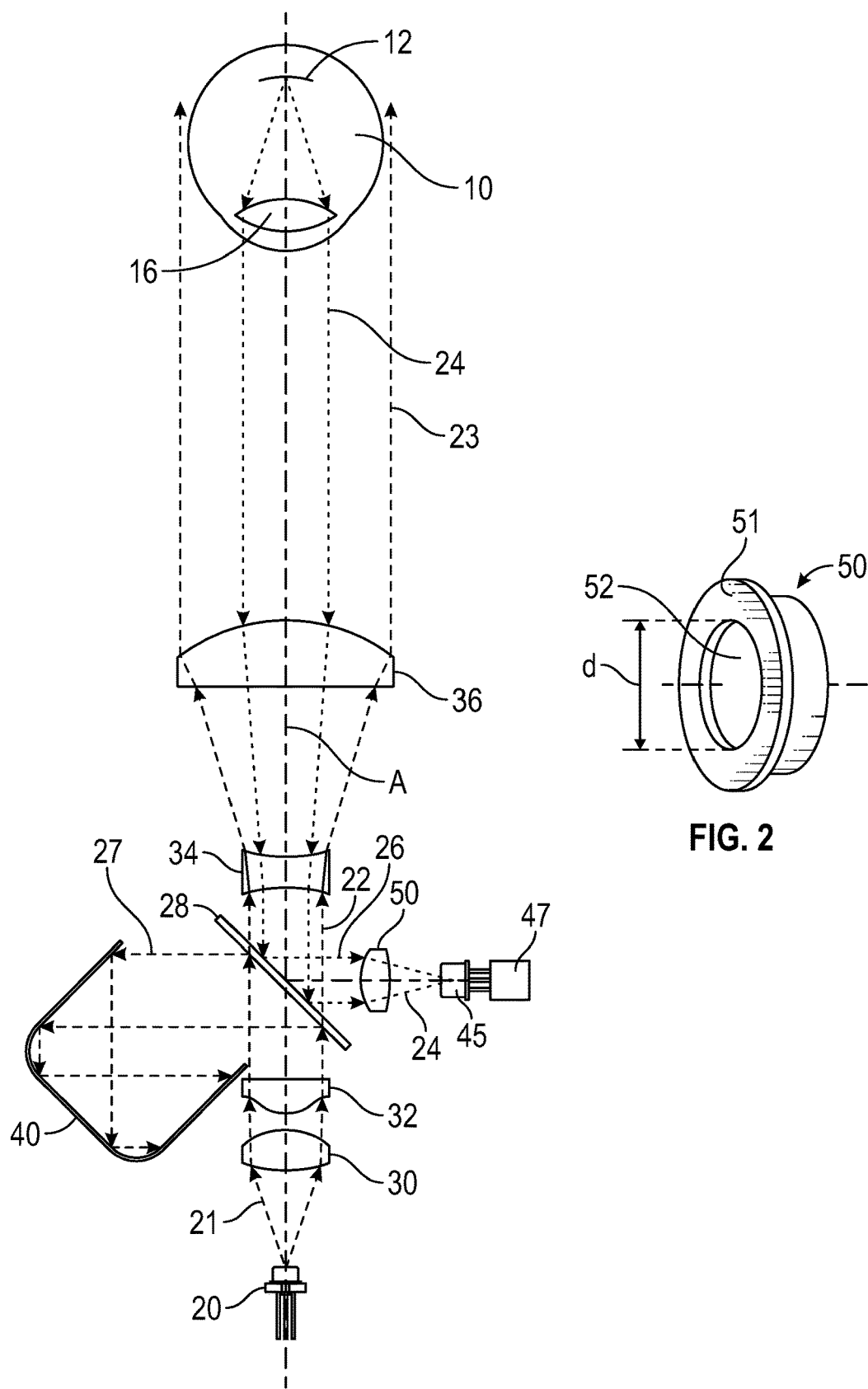
FIG. 1 is a schematic view diagrammatically depicting a system according to the present invention.
FIG. 2 is an enlarged perspective view of an eye safety lens component of the system shown in FIG. 1, illustrating that the safety lens has an aperture with a selected diameter dimension.

The presently disclosed apparatus and method are devised to protect the eyes of a user of a laser device from harm due to laser energy, especially laser energy inadvertently misdirected toward the eye. The invention provides an eye safety system and apparatus for lasers implemented, for example, within a device such as that described in U.S. Pat. No. 9,946,082. Nevertheless, this system may be integrated as a safety feature into many of various laser light-emitting devices. It is particularly contemplated that the system potentially may be incorporated into laser beam producing devices used for therapeutic applications of low-intensity laser energy such as, for example only, those disclosed in U.S. Pat. No. 8,136,531, 9,358,402, or 9,782,221.

Attention is invited to FIG. 1, which depicts diagrammatically a possible embodiment of the invention in operative association with a subject eyeball 10. A laser diode 20 produces a laser beam 21 that passes through the optics of the apparatus, and eventually may be (inadvertently) incidental upon the retina 12 of the eye 10. Laser light 23 passing through secondary lenses 34, 36 of the system may accidentally be directed toward the eyeball 10 of a user or bystander; when such an accident occurs, such incident light 23 of the main beam is retroflected by and from the eye 10 back toward the apparatus. FIG. 1 depicts that a beam of returning light 24 is reflected from the eye retina 12 back through an eye lens 16 of the eye 10. The returning beam 24 thus is retro-reflected from the eye 10, and eventually arrives at a detector 45 in the apparatus as described further hereinafter. The returning beam 24, having passed out from the eye lens 16, features parallel rays. Due partly to the parallel rays leaving from the eye lens 16, the returning beam 24 retro-reflected from the eye 10 has a higher intensity compared to light scattered from other surfaces (its intensity decreases with $R^2$, where R is the optical travel distance), back toward the optics mechanisms of the system. Also, in the near infrared (NIR) region, light is absorbed or transmitted easily by many body tissues, such that the body tissues scatter very little light. In comparison, NIR light is reflected better from the eye 10 than from other body tissues. Because this system is configured to collect the retro-reflected parallel light rays, it distinguishes light scattered from other surfaces (besides the retina 12) that does not pose a risk to eye damage. Moreover, because this system may be implemented in a device that uses NIR light, the system may further distinguish NIR light that has been retro-reflected from the eye 10.

An eye safety lens 50 directs the retro-reflected light beam 24 to the detector 45; there is a reflected portion 26 of the returning beam that is reflected from the second side of the beam splitter 28. It is observed that until the returning beam 24 (and its reflected portion 26) has passed the eye safety lens 50, the beam 24 is parallel to the rays of the incident main beam 23. Omitted for the sake of clarity from the side view of FIG. 1, but shown in FIG. 2, is that the eye safety lens 50 is provided with a screened aperture 52 of small diameter d such that only a beam of reflected light 26 having a corresponding diameter d is transmitted via the lens 50 to the detector 45.

According to the system and method of the embodiment seen in FIG. 1, the laser diode 20 emits a beam 21 in the infrared (IR) region, preferably such as in the near-infrared (NIR) region (approximately 750 nm to approximately 6,000 nm). The divergent beam 21 emitted from the diode source 20 passes through one or more primary lenses 30, 32 (two shown) to collimate the divergent beam 21 and to correct astigmatism. A dichroic beam splitter 28 passes a majority of any beam incident on a side thereof and reflects a minority of any such incident beam. Preferably, the dichroic beam splitter 28 has about 10-20% reflection, and is centered on an optical axis A, which central axis may correspond with the axis of the collimated, corrected laser beam. A first portion 22 of the collimated beam, a majority of the collimated beam, such as about 80-90% of the collimated beam, passes through the dichroic beam splitter 28 and is expanded and collimated again in one or more additional secondary lenses 34, 36 (two shown) to produce the main beam 23 (which may accidentally be incident on the eye 10). The dichroic beam splitter 28 reflects a narrow (less than 100 nanometer) wavelength band that includes the wavelength emitted from the laser diode source 20. The reflected portion 26 of light is in this narrow wavelength band. This reflected narrow wavelength band may be, for example, centered on the wavelength band of the light 21 emitted from the laser source 20.

The second side of the dichroic beam splitter 28 reflects onto the eye safety lens 50 the reflected portion 26 of the retroreflected returning beam 24. The opposite, first side of the dichroic beam splitter 28 also reflects a redirected portion 27 (e.g., 10-20%) of the collimated beam from the laser diode 20. In confronting relation to the eye safety lens 50 (i.e., on the other side of the beam splitter 28), a black light trap 40 is positioned to capture the redirected portion 27 of the collimated laser beam that is reflected from the first side of the beam splitter, thereby to reduce scattering of the redirected light 27 toward the eye safety detector 45. The black light trap 40 may be made, for example, of folded metal (e.g. aluminum) coated with a substance having a black matte color with very low reflectance; suitable light trapping techniques are known in the optical arts. The black light trap 40 may have its facets orthogonally arranged (at 90-degree relationships) so that the redirected portion 27 of the collimated light beam is not reflected toward the eye safety detector 45, as shown in FIG. 1. And being dichroic, the beam splitter 28 may be selectively configured to reflect mainly only a narrow (less than 100 nanometer) wavelength band onto the detector 45 in order to reduce, or even avoid, false alarms from other light sources (sun reflection, etc.)

In the event of an accidental direction of the main beam 23 into a subject eye 10, the returning beam 24, as retro-reflected from the retina 12, returns via the eye lens 16 to the second side of the beam splitter 28. The beam splitter 28 is placed to reflect the retro-reflected returning light 24 into a collecting lens (eye safety lens 50). The eye safety lens 50 has an infinity conjunction designed to collect retro-reflected light 26 and to focus it onto a fast detector 45. Per its properties described above, the dichroic beam splitter 28 thus reflects 10-20% of the retro-reflected beam 24 into the eye safety lens 50. Also, because the beam splitter 28 is dichroic, it reflects the narrow wavelength band (that includes the laser emission wavelength) into the eye safety lens 50.

Attention is invited to FIG. 2, showing an enlarged view of the eye safety lens 50. The eye-safety lens 50 may have a screen, cover, or other portion 51 defining a small aperture 52. The eye safety lens 50 also preferably is designed for receiving and collecting a retro-reflected beam 24 infinity-focused from the eye lens 16, that is, a beam composed mainly of parallel rays. This feature of the eye safety lens 50 is to capture mainly the retroreflected portion 26 of the retro-reflected light 24 and to reduce the capturing of extraneous scattered light.

For example, and referring to FIG. 2, the eye safety lens 50 preferably has some screen or portion 51 defining an aperture 52 with a small effective diameter d less than or equal to approximately 8 millimeters (mm), preferably within a range from about 5 mm to about 8 mm, inclusive. The cross-sectional area of the retro-reflected light beam 24 generally is smaller than that of the main beam 23 incident on the eye 10 and surrounding periocular tissue. This smaller area results from the retro-reflected light 24 having passed through the pupil (having a small diameter) of the subject eyeball 10. The eye safety lens 50 therefore preferably defines an aperture 52 having a diameter d approximating a diameter of a pupil of the eye 10. A normal pupil size in adult humans varies from about 1.5 mm to about 4 mm in diameter in bright light, and up to approximately 4 mm to approximately 8 mm diameter in dim light or the dark. Because the pupil varies in size (diameter) depending on light exposure, routine tests may be conducted to determine or optimize the aperture diameter d for the eye safety lens 50, so to be large enough to detect eye retroreflection, yet small enough to reduce, or even eliminate, false alarms from light other than eye retroreflection (e.g., reflected portion 26). Again, the aperture diameter d for the eye safety lens 50 accordingly may be, for example, about equal to the average pupil diameter of adult humans in medium light, e.g., from about 5 mm to about 8 mm, and preferably, by way of further example, approximately 4 mm; the effective aperture 52 diameter d preferably is as small as possible while still permitting retroreflection detection.

The fast detector 45 is connected to an amplifier and comparator circuitry assembly 47 to identify the retro-reflected signal received from the detector. If and when a retroflection signal is identified to be consequent to light retro-reflected from the subject eye 10, the comparator circuitry assembly 47 of the system immediately signals an interruption of laser diode function (e.g., by interrupting power to the diode 20)—thereby promptly terminating laser emission from source 20. The comparator circuitry assembly 47 includes or communicates with a switching means of any suitable type, so that the interruption signal generated by the comparator assembly 47 actuates the switch in the assembly 47 to turn off the laser diode 20. Alternatively to a comparator, the detector 45 alternatively can be connected to an amplifier, analog-to-digital (ATD) converter, or voltage-to-frequency (VTF) converter and microprocessor assembly 47 (in lieu of a comparator assembly) that shuts off emission from the source 20 upon receiving the retro-reflected light signal.

The reflective characteristic of the beam splitter 28 may be adaptively selected in accordance with the intensity of the eye's retro-reflected light in the corresponding laser wavelength. For example, the human eye has much higher retroflection in infrared wavelengths than in the green wavelengths; consequently, NIR lasers may use a lower-reflection beam splitter 28 than for a green laser, which may be included in the device according to the description in U.S. Pat. No. 9,946,082.

As example, an eye safety system includes a light detector 45 coupled to a laser diode 20 in a manner that enables turning off the laser diode 20 after the detector detects a selected intensity of light in a selected wavelength. A dichroic beam splitter 28 in a beam path of the laser diode 20 is configured to pass light 21 from the laser diode and to reflect the returning light 24 returned along the path of the main beam 23. The laser source 20, beam splitter 28, at least one primary lens 30 and at least one secondary lens 34 in one embodiment are in mutual alignment along a central optical axis A. The beam splitter 28 is configured to reflect to the detector 45 only light in a particular wavelength band of less than 100 nm but including the selected wavelength, and to minimize reflection to the detector of light outside the narrow wavelength band. A substantially infinity-focused safety lens 50 collects light 26 reflected from the beam splitter 28 and passes the reflected light 26 onto the detector 45.

As a further example, in combination with the infinity-focus, the safety lens 50 has an aperture 52 sized to capture mainly retro-reflected light in a beam 24 returning from the eye 10, that is, light parallel to the path of the main beam 23.

As a still further example, the eye safety system and method include a black light trap 40 positioned to capture light 27, from the laser diode 20, that is reflected from the second side of the beam splitter 28 in a direction away from the detector 45.

Although specific embodiments have been illustrated and described in this specification, it will be appreciated by those of ordinary skill in the art that any arrangement that is calculated to achieve the same purpose may be substituted for the specific embodiment shown. This application is intended to cover any adaptations or variations of the present invention. For example, modification of the optics by means of differing hardware or alternative lens configurations may be applied. Further, adding variations of materials and lens/beam slitter configurations in combination or alone which increase the ability of the system to detect and process signals from laser light energy retro-reflected from a human eye should be considered without limitation.

What is claimed is:

1. An eye safety apparatus for laser devices, adapted to detect laser light retroreflected from an eye and to shut down a laser source in a short time when the retroreflected light is detected, comprising, to distinguish between light retroreflected from the eye and extraneous scattered light:

a laser light detector;

a safety lens defining an aperture having a diameter less than or equal to approximately 8 mm approximating a diameter of a pupil of a human eye in dim light or the dark;

a dichroic beam splitter which reflects to the safety lens a reflected beam of light from the eye having a narrow wavelength band including a wavelength emitted from the laser source; and a black light trap to capture a redirected beam reflected from the beam splitter to reduce beam reflection toward the safety lens;

wherein the safety lens is in infinite conjunction for collecting and focusing on the detector any parallel light beam retroreflected from the eye, but not the scattered light.

2. The apparatus of claim 1 wherein a first portion of the beam emitted from the laser source passes through the beam splitter and a second, the redirected, portion of the emitted beam is reflected from a first side of the beam splitter; and wherein the first portion of the beam may accidentally be directed to the eye and retroreflected from the eye and toward the beam splitter.

3. The apparatus of claim 2 wherein the dichroic beam splitter passes a majority of any incident beam.

4. The apparatus of claim 3 wherein the first portion of the emitted beam is between 80% and 90% of the emitted beam, and the redirected portion of the emitted beam is between 10% and 20% of the emitted beam.

5. The apparatus of claim 3 wherein the dichroic beam splitter reflects a narrow wavelength band of less than 100 nm that includes the wavelength emitted from the source.

6. The apparatus of claim 2 wherein the eye safety lens directs to the detector at least a portion of any laser light retroreflected from the eye and reflected from a second side of the beam splitter.

7. The apparatus of claim 6 further comprising an amplifier and comparator assembly, in communication with the detector, for identifying a retroreflection signal from the detector and switching off the laser source.

8. The apparatus of claim 1 wherein the aperture diameter is between 5 mm and 8 mm, inclusive.

9. A safety system for use with a laser source, the system adapted to protect a user's eye from harm due to laser light directed toward the eye, and comprising, to distinguish between laser light retroreflected from the eye and extraneous scattered light:

at least one primary lens for collimating into a collimated beam a divergent beam emitted from the source;

a dichroic beam splitter for splitting the collimated beam, whereby a first portion of the collimated beam passes through the beam splitter and a second, redirected, portion of the collimated beam is reflected from a first side of the beam splitter;

a light trap for capturing the redirected portion of the collimated laser beam;

at least one secondary lens for expanding and collimating into a main beam the first portion of the collimated beam;

a laser light detector;

an eye safety lens, in infinite conjunction and defining an aperture having a diameter less than or equal to approximately 8 mm, for collecting and focusing on the detector not the scattered light but only any returning light beam retroreflected from the eye and reflected from a second side of the beam splitter; and an amplifier and comparator assembly, in communication with the detector, for:

identifying a retroreflection signal from the detector; and switching off the laser source;

wherein when a returning beam is retroflected from the user's eye, it is directed to and detected by the detector, which detector generates a retroflection signal to the amplifier and comparator assembly to switch off the laser source.

10. The system of claim 9 wherein the eye safety lens defines an aperture having a diameter approximating a diameter of a pupil of the eye.

11. The system of claim 10 wherein the aperture diameter is between 5 mm and 8 mm, inclusive.

12. The system of claim 9 wherein the dichroic beam splitter passes a majority of a beam incident thereon.

13. The system of claim 12 wherein the first portion of the collimated beam is between 80% and 90% of the beam emitted from the source, and the redirected portion of the emitted beam is between 10% and 20% of the beam emitted from the source.

14. The system of claim 12 wherein the dichroic beam splitter reflects a narrow wavelength band of less than 100 nm that includes a wavelength emitted from the source.

* * * * *